United States Patent
Gharib

(10) Patent No.: US 11,406,264 B2
(45) Date of Patent: Aug. 9, 2022

(54) NON-INVASIVE MEASUREMENT OF INTRAOCULAR PRESSURE

(71) Applicant: CALIFORNIA INSTITUTE OF TECHNOLOGY, Pasadena, CA (US)

(72) Inventor: Morteza Gharib, Altadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 66 days.

(21) Appl. No.: 15/414,497

(22) Filed: Jan. 24, 2017

(65) Prior Publication Data

US 2017/0209046 A1 Jul. 27, 2017

Related U.S. Application Data

(60) Provisional application No. 62/286,782, filed on Jan. 25, 2016.

(51) Int. Cl.
*A61B 3/16* (2006.01)
*A61B 3/00* (2006.01)
*A61B 3/12* (2006.01)
*A61B 3/14* (2006.01)

(52) U.S. Cl.
CPC ............ *A61B 3/165* (2013.01); *A61B 3/0025* (2013.01); *A61B 3/1241* (2013.01); *A61B 3/145* (2013.01); *A61B 3/16* (2013.01); *A61B 2560/0223* (2013.01)

(58) Field of Classification Search
CPC ......... A61B 3/165; A61B 3/16; A61B 3/0025; A61B 3/1241; A61B 3/145; A61B 2560/0223
See application file for complete search history.

(56) References Cited

U.S. PATENT DOCUMENTS

| | | |
|---|---|---|
| 3,069,654 A | 12/1962 | Hough |
| 4,101,917 A | 7/1978 | Ueda |
| 4,264,921 A | 4/1981 | Pennington et al. |
| 4,512,656 A | 4/1985 | Shinoda et al. |
| 4,650,466 A | 3/1987 | Luther |
| 4,727,471 A | 2/1988 | Driels et al. |

(Continued)

FOREIGN PATENT DOCUMENTS

| | | |
|---|---|---|
| EP | 1175106 A2 | 1/2002 |
| GB | 2242270 A | 3/1991 |

(Continued)

OTHER PUBLICATIONS

Zhang et al. "A survey on computer aided diagnosis for ocular diseases", BMC Medical Informatics and Decision Making 2014, 14:80 http://www.biomedcentral.com/1472-6947/14/80 (Year: 2014).*

(Continued)

*Primary Examiner* — Tse W Chen
*Assistant Examiner* — Avery M Foley
(74) *Attorney, Agent, or Firm* — One LLP

(57) ABSTRACT

Devices, systems and methods are described for non-invasively monitoring and/or measuring or estimating intraocular pressure. Medical or diagnostic methods embodiments described herein include high resolution imaging of the sclera of one or both of a patient's eyes using digital photography or videography. The hardware employed may be for two-dimensional (2D) or three-dimensional (3D) imaging.

8 Claims, 2 Drawing Sheets

(56) References Cited

U.S. PATENT DOCUMENTS

| | | | |
|---|---|---|---|
| 4,879,664 A | 11/1989 | Suyama et al. | |
| 4,948,258 A | 8/1990 | Caimi | |
| 5,018,854 A | 5/1991 | Rioux | |
| 5,031,154 A | 7/1991 | Watanabe | |
| 5,071,407 A | 12/1991 | Termin et al. | |
| 5,075,561 A | 12/1991 | Rioux | |
| 5,168,327 A | 12/1992 | Yamawaki | |
| 5,206,498 A | 4/1993 | Sensui | |
| 5,216,695 A | 6/1993 | Ross et al. | |
| 5,222,971 A | 6/1993 | Willard et al. | |
| 5,235,857 A | 8/1993 | Anderson | |
| 5,270,795 A | 12/1993 | Blais | |
| 5,327,880 A | 7/1994 | Harley et al. | |
| 5,351,078 A | 9/1994 | Lemelson | |
| 5,373,151 A | 12/1994 | Eckel, Jr. et al. | |
| 5,476,100 A | 12/1995 | Galel | |
| 5,496,277 A | 3/1996 | Termin et al. | |
| 5,527,282 A | 6/1996 | Segal | |
| 5,579,444 A | 11/1996 | Dalziel et al. | |
| 5,604,344 A | 2/1997 | Finarov | |
| 5,714,762 A | 2/1998 | Li et al. | |
| 5,745,067 A | 4/1998 | Chou et al. | |
| 5,810,005 A * | 9/1998 | Dublin, Jr | A61B 5/021 600/398 |
| 5,864,359 A | 1/1999 | Kazakevich | |
| 5,922,961 A | 7/1999 | Hsu et al. | |
| 5,928,260 A | 7/1999 | Chin et al. | |
| 5,986,694 A | 11/1999 | Ilino | |
| 6,045,623 A | 4/2000 | Cannon | |
| 6,112,029 A | 8/2000 | Suda | |
| 6,115,553 A | 9/2000 | Iwamoto | |
| 6,157,747 A | 12/2000 | Szeliski et al. | |
| 6,229,913 B1 | 5/2001 | Nayar et al. | |
| 6,229,959 B1 | 5/2001 | Suda et al. | |
| 6,262,803 B1 | 7/2001 | Hallerman et al. | |
| 6,271,918 B2 | 8/2001 | Blais | |
| 6,278,847 B1 | 8/2001 | Gharib et al. | |
| 6,304,284 B1 | 10/2001 | Dunton et al. | |
| 6,344,048 B1 | 2/2002 | Chin et al. | |
| 6,519,359 B1 | 2/2003 | Nafis et al. | |
| 6,545,701 B2 | 4/2003 | Sinclair et al. | |
| 6,563,543 B1 | 5/2003 | Doron | |
| 6,711,293 B1 | 3/2004 | Lowe | |
| 6,748,112 B1 | 6/2004 | Nguyen et al. | |
| 6,750,904 B1 | 6/2004 | Lambert | |
| 6,765,569 B2 | 7/2004 | Neumann et al. | |
| 6,912,293 B1 | 6/2005 | Korobkin | |
| 6,915,008 B2 | 7/2005 | Barman et al. | |
| 6,943,349 B2 | 9/2005 | Adamec et al. | |
| 6,955,656 B2 | 10/2005 | Bergheim et al. | |
| 6,965,690 B2 | 11/2005 | Matsumoto | |
| 7,006,132 B2 | 2/2006 | Pereira et al. | |
| 7,106,375 B2 | 9/2006 | Venturino et al. | |
| 7,171,054 B2 | 1/2007 | Fiete et al. | |
| 7,236,622 B2 | 6/2007 | Chen et al. | |
| 7,260,274 B2 | 8/2007 | Sawhney et al. | |
| 7,271,377 B2 | 9/2007 | Mueller et al. | |
| 7,340,077 B2 | 3/2008 | Gokturk et al. | |
| 7,372,642 B2 | 5/2008 | Rohaly et al. | |
| 7,423,666 B2 | 9/2008 | Sakakibara et al. | |
| 7,496,226 B2 | 2/2009 | Negahdaripour et al. | |
| 7,565,029 B2 | 7/2009 | Zhou et al. | |
| 7,605,817 B2 | 10/2009 | Zhang et al. | |
| 7,612,869 B2 | 11/2009 | Pereira et al. | |
| 7,612,870 B2 | 11/2009 | Graff et al. | |
| 7,668,388 B2 | 2/2010 | Bryll | |
| 7,715,018 B2 | 5/2010 | Gharib et al. | |
| 7,715,918 B2 | 5/2010 | Melvin | |
| 7,747,151 B2 | 6/2010 | Kochi et al. | |
| 7,819,591 B2 | 10/2010 | Rohaly et al. | |
| 7,826,067 B2 | 11/2010 | Gharib et al. | |
| 7,894,078 B2 | 2/2011 | Gharib et al. | |
| 7,916,309 B2 | 3/2011 | Gharib et al. | |
| 8,089,635 B2 | 1/2012 | Gharib et al. | |
| 8,179,424 B2 | 5/2012 | Moller | |
| 8,190,020 B2 | 5/2012 | Numako et al. | |
| 8,401,276 B1 | 3/2013 | Choe et al. | |
| 8,472,032 B2 | 6/2013 | Gharib et al. | |
| 8,514,268 B2 | 8/2013 | Gharib et al. | |
| 8,576,381 B2 | 11/2013 | Gharib et al. | |
| 8,619,126 B2 | 12/2013 | Gharib et al. | |
| 8,773,507 B2 | 7/2014 | Gharib et al. | |
| 9,530,213 B2 | 12/2016 | Gharib et al. | |
| 2001/0031920 A1 | 10/2001 | Kaufman et al. | |
| 2002/0038120 A1 | 3/2002 | Duhaylongsod et al. | |
| 2003/0025811 A1 | 2/2003 | Keelan et al. | |
| 2003/0096210 A1 | 5/2003 | Rubbert et al. | |
| 2003/0125719 A1 | 7/2003 | Furnish | |
| 2003/0160970 A1 | 8/2003 | Basu et al. | |
| 2003/0210407 A1 | 11/2003 | Xu | |
| 2004/0136567 A1 | 7/2004 | Billinghurst et al. | |
| 2004/0155975 A1 | 8/2004 | Hart et al. | |
| 2005/0025116 A1 | 2/2005 | Chen et al. | |
| 2005/0104879 A1 | 5/2005 | Kaye et al. | |
| 2005/0119684 A1 | 6/2005 | Guterman et al. | |
| 2005/0168616 A1 | 8/2005 | Rastegar et al. | |
| 2005/0251116 A1 | 11/2005 | Steinke et al. | |
| 2005/0264668 A1 | 12/2005 | Miyamoto | |
| 2006/0044546 A1 | 3/2006 | Lewin et al. | |
| 2006/0092314 A1 | 5/2006 | Silverstein et al. | |
| 2006/0098872 A1 | 5/2006 | Seo et al. | |
| 2006/0209193 A1 | 9/2006 | Pereira et al. | |
| 2006/0228010 A1 | 10/2006 | Rubbert et al. | |
| 2006/0285741 A1 | 12/2006 | Subbarao | |
| 2007/0008312 A1 | 1/2007 | Zhou et al. | |
| 2007/0031064 A1 | 2/2007 | Zhao et al. | |
| 2007/0056768 A1 | 3/2007 | Hsieh et al. | |
| 2007/0076090 A1 | 4/2007 | Alexander | |
| 2007/0078500 A1 | 4/2007 | Ryan et al. | |
| 2007/0146700 A1 | 6/2007 | Kowarz et al. | |
| 2007/0188769 A1 | 8/2007 | Rohaly et al. | |
| 2007/0195162 A1 | 8/2007 | Graff et al. | |
| 2007/0236694 A1 | 10/2007 | Gharib et al. | |
| 2008/0031513 A1 | 2/2008 | Hart | |
| 2008/0091691 A1 | 4/2008 | Tsuji | |
| 2008/0180436 A1 | 7/2008 | Kraver | |
| 2008/0201101 A1 | 8/2008 | Hebert et al. | |
| 2008/0218604 A1 | 9/2008 | Shikano et al. | |
| 2008/0239316 A1 | 10/2008 | Gharib et al. | |
| 2008/0259354 A1 | 10/2008 | Gharib et al. | |
| 2008/0278570 A1 | 11/2008 | Gharib et al. | |
| 2008/0278572 A1 | 11/2008 | Gharib et al. | |
| 2008/0278804 A1 | 11/2008 | Gharib et al. | |
| 2009/0016642 A1 | 1/2009 | Hart | |
| 2009/0129667 A1 | 5/2009 | Ho et al. | |
| 2009/0189830 A1* | 7/2009 | Deering | G09G 3/02 345/1.3 |
| 2009/0238449 A1 | 9/2009 | Zhang et al. | |
| 2010/0007718 A1 | 1/2010 | Rohaly, Jr. et al. | |
| 2010/0094138 A1 | 4/2010 | Gharib et al. | |
| 2011/0074932 A1 | 3/2011 | Gharib et al. | |
| 2013/0211285 A1 | 8/2013 | Fuller et al. | |
| 2014/0073917 A1* | 3/2014 | Huang | A61B 5/0066 600/427 |
| 2016/0051145 A1* | 2/2016 | Rickard | A61B 3/16 600/399 |

FOREIGN PATENT DOCUMENTS

| | | |
|---|---|---|
| JP | 2655885 B2 | 9/1997 |
| JP | 2002-220991 | 8/2002 |
| JP | 2002-254708 | 9/2002 |
| JP | 2003-289293 | 10/2003 |
| JP | 2004-191240 | 7/2004 |
| WO | WO 88/00710 A1 | 1/1988 |
| WO | WO 00/69357 A1 | 11/2000 |
| WO | WO 01/86281 A1 | 11/2001 |
| WO | WO 02/096478 A2 | 12/2002 |
| WO | WO 2006/009786 A2 | 1/2006 |
| WO | WO 2007/041542 A2 | 4/2007 |
| WO | WO 2007/056768 A2 | 5/2007 |
| WO | WO 2007/095307 A1 | 8/2007 |
| WO | WO 2007/130122 A2 | 11/2007 |
| WO | WO 2008/091691 A1 | 7/2008 |

(56) References Cited

FOREIGN PATENT DOCUMENTS

OTHER PUBLICATIONS

Bando, Y., "How to Disassemble the Canon EF 50mm f/1.8 II Lens", 2008, pp. 1-21.
Battle, J., et al., "Recent Progress in Coded Structured Light as a Technique to Solve the Correspondence Problem: a Survey", Pattern Recognition, 1998, vol. 31, No. 7, pp. 963-982.
Chang, N.L., Efficient Dense Correspondences using Temporally Encoded Light Patterns, IEEE, Oct. 12, 2003.
Dellaert, F., et al., Structure from Motion without Correspondence, Computer Vision & Pattern Recoqnition, 2000.
El-Hakim S.F., et al., A System for Indoor 3-D Mapping and Virtual Environments, Proceedings of the SPIE, 1997.
Favaro, P., et al., "Observing Shape from Defocused Images", Int'l Journal of Computer Vision, vol. 52, No. 1, 2003, pp. 25-43.
Guarnieri, A., et al., "3D Modeling of Real Artistic Objects with Limited Computers Resources", Proc. Of XVIII CIPA Symposium on Architectural & Archaeoloqical Photoqrammetry, Oct. 1999.
Hasinoff, S.W, "Variable-Aperture Photography", Graduate Department of Computer Science, University of Toronto, Thesis submitted in 2008, pp. 1-180.
Horn, E., et al., Toward Optimal Structured Light Patterns, 3DIM, 1997.
Horstmeyer, R., et al., "Pupil plane multiplexing for multi-domain imaging sensors", Proc. SPIE 7096, Adaptive Coded Aperture Imaging and Non-Imaging Sensors II, 2008.
Kießling, A.,"A Fast Scanning Method for Three-Dimensional Scenes", IEEE Proceedings $3^{rd}$ International Conference on Pattern Recognition, 1976, pp. 586-589.
Koninckx, T.P., et al., A Graph Cut based Adaptive Structured Light approach for real-time Ranqe Acquisition, 3EDPVT, 2004.
Kordelas, G., et al., State-of-the-art Algorithms for Complete 3D Model Reconstruction, "Enqaqe" Summer School, 2010.
Lepetit, V., et al., "Monocular Model-Based 3D Tracking of Rigid Objects: A Survey", Foundation and Trends in Computer Graphics and Vision, vol. 1, No. 1, 2005, pp. 1-89.
Levenberg, K., "A Method for the Solution of Certain Non-Linear Problems in Least Squares", Quarterly of Applied Mathematics, vol. II, No. 2, Jul. 1944.
Levin, A., et al., "Image and Depth from a Conventional Camera with a Coded Aperture", ACM Transactions on Graphics, vol. 26, No. 3, Jul. 1999, pp. 70-71-70-9.
Li, S.Z., Markov Random Field Models in Computer Vision, Springer-Verlag, 1995.
Lowe, D.G., Three-Dimensional Object Recognition from Single Two-Dimensional Images, Artificial Intelligence, vol. 31, No. 3, Mar. 1987, pp. 355-395.
Lowe, D.G., Object Recognition from Local Scale-Invariant Features, Proc. of the Int'l Conference on Computer Vision, Sep. 1999.
Makadia, A., et al., Fully Automatic Registration of 3D Point Clouds, Proceedings of the 2006 IEEE Computer Society Conference on Computer Vision and Pattern Recoqnition, 2006.
Marquardt, D.W., An Algorithm for Least-Squares Estimation of Nonlinear Parameters, Journal of the Society for Industrial and Applied Mathematics, vol. 11, No. 2, Jun. 1963, pp. 431-441.
Mouaddib, E., et al., Recent Progress in Structured Light in order to Solve the Correspondence Problem in Stereo Vision, Proceedinqs of the 1997 IEEE, Apr. 1997.
Neugebauer, P.J., Geometrical Cloning of 3D Objects via Simultaneous Registration of Multiple Ranqe Imaqes, Shape Modelinq & Application, Mar. 1997.
Nguyen, V.A., et al., Detection of the depth order of defocused images, Vision Research 45, 2005, pp. 1003-1011.
Pagés, J., et al., "Implementation of a Robust Coded Structured Light Technique for Dynamic 3D Measurements", ICIP, 2003.
Pereira, F., et al., "Two-frame 3D particle tracking", Measurement Science and Technology, vol. 17, 2006, pp. 1680-1692.
Raji, A., et al., "PixelFlex2: A Comprehensive, Automatic, Casually-Aligned Multi-Projector Display", PROCAMS, 2003.
Raskar, R., et al., Multi-Projector Displays Using Camera-Based Registration, IEEE Visualization, 1999.
Rocchini, C., et al., A low cost 3D scanner based on structured light, Computer Graphics Forum (Euroqraphics 2001 Conf. Issue).
Rusinkiewicz, S., et al., Real-Tiime 3D Model Acguisition, ACM Transactions on Graphics, 2002.
Salvi, J., et al., Pattern codification strategies in structured light systems, Pattern Recognition, 2004.
Scharstein, D., et al., A Taxonomy and Evaluation of Dense Two-Frame Stereo Correspondence Algorithms, IJCV, 2002.
Scharstein, D., et al., "High-Accuracy Stereo Depth Maps Using Structured Light", IEEE Computer Society Conf. on Computer Vision and Pattern Recognition, 2003, vol. 1, pp. 195-202.
Sinofsky, "Measurement of Laser Beam Spreading in Biological Tissue Scattering", SPIE, vol. 712, Lasers in Medicine (1986).
Smith, E.R., et al., "Registration of combined range-intensity scans: Initialization through Verification", Computer Vision and Imaqe Understandinq, vol. 110, 2008, pp. 226-244.
Subbarao, M., et al., "Analysis of Defocused Image Data for 3D Shape Recovery using a Reqularization Technique", SPIE, 1997.
Tardif, J., "Multi-projectors for arbitrary surfaces without explicit calibration and reconstruction", DIM, 2003.
Tardif, J., et al., "A MRF formulation for coded structured light", Proceedings of the $5^{th}$ Int'l Conf. on 3-D Diqital Imaqinq & Modelinq, 2005.
Wang, Z., et al., "Extraction of the Corner of Checkerboard image", Proceedings of the 7th World Conqress on Intelliqent Control and Automation, Jun. 25-27, 2008.
Weisstein, E., Gray Code, http://mathworld.wolfram.com/GrayCode.html.
Willert, C.E., et al., "Three-dimensional particle imaging with a single camera", Experiments in Fluids, vol. 12, 1992, pp. 353-358.
Williams, J.A., et al., "Multiple View 3D Registration: A Review and a New Technique", Systems Man. & Cybernetics, vol. 10, 1999.
Wu, M., et al., "Three-dimensional fluorescent particle tracking at micron-scale using a single Camera", Experiments in Fluids, 2005, pp. 461-465.
Yang, R., et al., PixelFlex: A Reconfigurable Multi-Projector Display System, IEEE Visualization, 2001.
Zhang, S., et al., High-resolution, Real-time 3D Shape Acquisition, IEEE Workshop of real-time 3D sensors & their uses, 2004.
AU, 2008244494 Examiner's First Report, dated Aug. 18, 2020.
WO, PCT/US2007/008598 ISR and Written Opinion, dated Apr. 11, 2008.
WO, PCT/US2008/000991 ISR and Written Opinion, dated May 21, 2008.
WO, PCT/US2008/000882 ISR and Written Opinion, dated Mar. 20, 2009.
WO, PCT/US2008/005311 ISR and Written Opinion, dated Sep. 8, 2008.
WO, PCT/US2008/005313 ISR and Written Opinion, dated Sep. 8, 2008.
WO, PCT/US2008/005314 ISR and Written Opinion, dated Sep. 8, 2008.
WO, PCT/US2008/005315 ISR and Written Opinion, dated Sep. 8, 2008.
WO, PCT/US2008/012947 ISR and Written Opinion, dated Jul. 14, 2009.
WO, PCT/US2009/003167 ISR and Written Opinion, dated Oct. 29, 2010.
WO, PCT/US2009/004362 ISR and Written Opinion, dated Apr. 8, 2010.
WO, PCT/US2010/046908 ISR and Written Opinion, dated Apr. 29, 2011.
WO, PCT/US2010/057532 ISR and Written Opinion, dated Oct. 25, 2011.
WO, PCT/US2011/032580 ISR and Written Opinion, dated Jul. 7, 2011.
WO, PCT/US2012/046557 ISR and Written Opinion, dated Oct. 2, 2012.
WO, PCT/US2012/046484 ISR and Written Opinion, dated Sep. 24, 2012.

(56) References Cited

OTHER PUBLICATIONS

WO, PCT/US2017/014771 ISR and Written Opinion, dated Apr. 20, 2017.

* cited by examiner

NON-INVASIVE MEASUREMENT OF INTRAOCULAR PRESSURE

RELATED APPLICATIONS

This filing claims the benefit of and priority to U.S. Provisional Application Ser. No. 62/286,782 filed Jan. 25, 2016, which is incorporated by reference herein in its entirety for all purposes.

FIELD

Devices, systems and methods are described for non-invasively measuring Intraocular Pressure (IOP).

BACKGROUND

Glaucoma is associated with elevated Intraocular Pressure (IOP). In this respect, monitoring IOP is an important task when it is crucial to inform patients and doctors about stages of the disease as well methods to be used for intervention and therapeutic approaches.

Current IOP measurement techniques are invasive and usually include direct contact with sclera either by touching it by an applicator or using air jets to create local pressure. The main objective of each approach is to create a physical depression that can be measured and used to estimate IOP through pre-determined data for given age, gender.

However, there are general assumptions about sclera's geometrical and mechanical properties that may not necessarily apply to a given patient. In this respect large variation in reading IOP even in clinical setting is expected from current approaches. Improvement is needed and addressed by embodiments of the present invention.

SUMMARY

A non-invasive patient-specific optical technique is described to estimate IOP. This estimate (also referred to herein as a measurement) can utilize the characteristic that blood vessel patterns (BVP) are unique to each individual, similar to fingerprint patterns. The other characteristic that can be relied upon is that an eyeball's volume and surface change as a response to changes in IOP. Accordingly, while blood vessel patterns retain their geometrical similarity, their scale changes as the eyeball shrinks or expands in response to changes in IOP.

Medical or diagnostic methods embodiments described herein include high resolution imaging of the sclera of one or both of a patient's eyes using digital photography or videography. The hardware employed may be for two-dimensional (2D) or three-dimensional (3D) imaging. For the latter, multiple cameras for stereo imaging or a single camera for defocus-type imaging or blur-based imaging may be employed. Further details are provided below.

Employing commercially available Scale Invariant Feature Transform (SIFT) software (e.g., as described in U.S. Pat. No. 6,711,293), generic micro and macro feature based matching and stitching techniques, or other image stitching methods, 2D or 3D images of sclera(s) are reconstructed that include blood vessel patterns. In selecting imaging hardware, advantages of higher accuracy may favor 3D modeling in system design. Yet, 2D approaches may be useful, at least in producing rough estimates.

Pattern recognition techniques are, optionally, then used to identify blood vessel patterns in the 2D or 3D reconstruction or model. Standard Hough Transform (e.g., as described in U.S. Pat. No. 3,069,654), a Histogram of Oriented Gradients (HOG) or other methodology as well know in the art may be employed for the pattern recognition.

Then, pattern matching of the image(s) with previous patient BVP is performed, and estimation of scale change. A standard Digital Image Correlation (DIC) or Cross-Correlation (CC) technique can be used.

Prior to the above, set of calibration points (a minimum of two points for each eye of a given patient) are obtained once. This may be done by and ophthalmologists using pressure modifying eye drops and imaging, 2D or 3D reconstruction, and pattern recognition, as well as standard tonometry to establish pressure BVP size relationship. Comparing the scale change calculated per above with the calibration data provides a measurement or estimated of IOP.

Alternatively, after an initial measurement session, an given (sometimes, arbitrary) value can be ascribed to the volume of the eye and subsequent relative volumes can be compared to this baseline data or to each other to determine if there is a trend or measurable change in ocular volume or warping. In this case, use of 3D imaging may be particularly beneficial as offering a more direct (at least partial) estimate of volume, although 2D imaging can still be used when making assumptions regarding the anatomy (e.g., that its geometry remains consistent in shape as size changes).

As such, a pressure-volume relationship may be used in the subject embodiments instead of patient-specific BVP. However, it is not a preferred approach since in those methods the underlying assumption is that the eye-ball has a spherical geometry which in general does not hold well. Nevertheless, when the intention is monitoring changes, alone, instead of true or pure IOP estimation or measurement, such an approach can be useful (e.g., as in providing an alert or "flagging" a change in condition of a patient that warrants caution, study or further testing).

In the various approaches above, the sclera of the eye is imaged. Alternatively, images of the main retinal blood vessels in the center of the very back inner wall of the eye seen in a typical fundus photo can be used in a similar fashion described above to obtain IOP.

The subject devices or systems, kits in which they are included (with and without assembly), methods of use (software methods and/or medical methods) are all within the scope of the present disclosure. Some aspects of the same are described above and more detailed discussion is presented in connection with the figures below.

Various systems, devices, methods, features and advantages of the subject matter described herein will be or will become apparent to one with skill in the art upon examination of the following figures and Detailed Description. It is intended that all such systems, devices, methods, features and advantages be included within this description, be within the scope of the subject matter described herein and be protected or protectable by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

It should be noted that all features, elements, components, functions, acts and steps described with respect to any embodiment provided herein are intended to be freely combinable and substitutable with those from any other embodiment. If a certain feature, element, component, function, act or step is described with respect to only one embodiment, then it should be understood that that feature, element, component, function, act or step can be used with every other embodiment described herein unless explicitly stated otherwise. This paragraph therefore serves as antecedent basis and written support for the introduction of claims, at any time, that combine features, elements, components, functions, acts and steps from different embodiments, or that substitute features, elements, components, functions, acts and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Various example embodiments are described below. Reference is made to these examples in a non-limiting sense. They are provided to illustrate more broadly applicable aspects of inventive aspects. Various changes may be made to the embodiments described and equivalents may be substituted without departing from their true spirit and scope. In addition, many modifications may be made to adapt a particular situation, material, composition of matter, process, process act(s) or step(s) to the objective(s), spirit or scope of the claims made herein.

Figure 1:
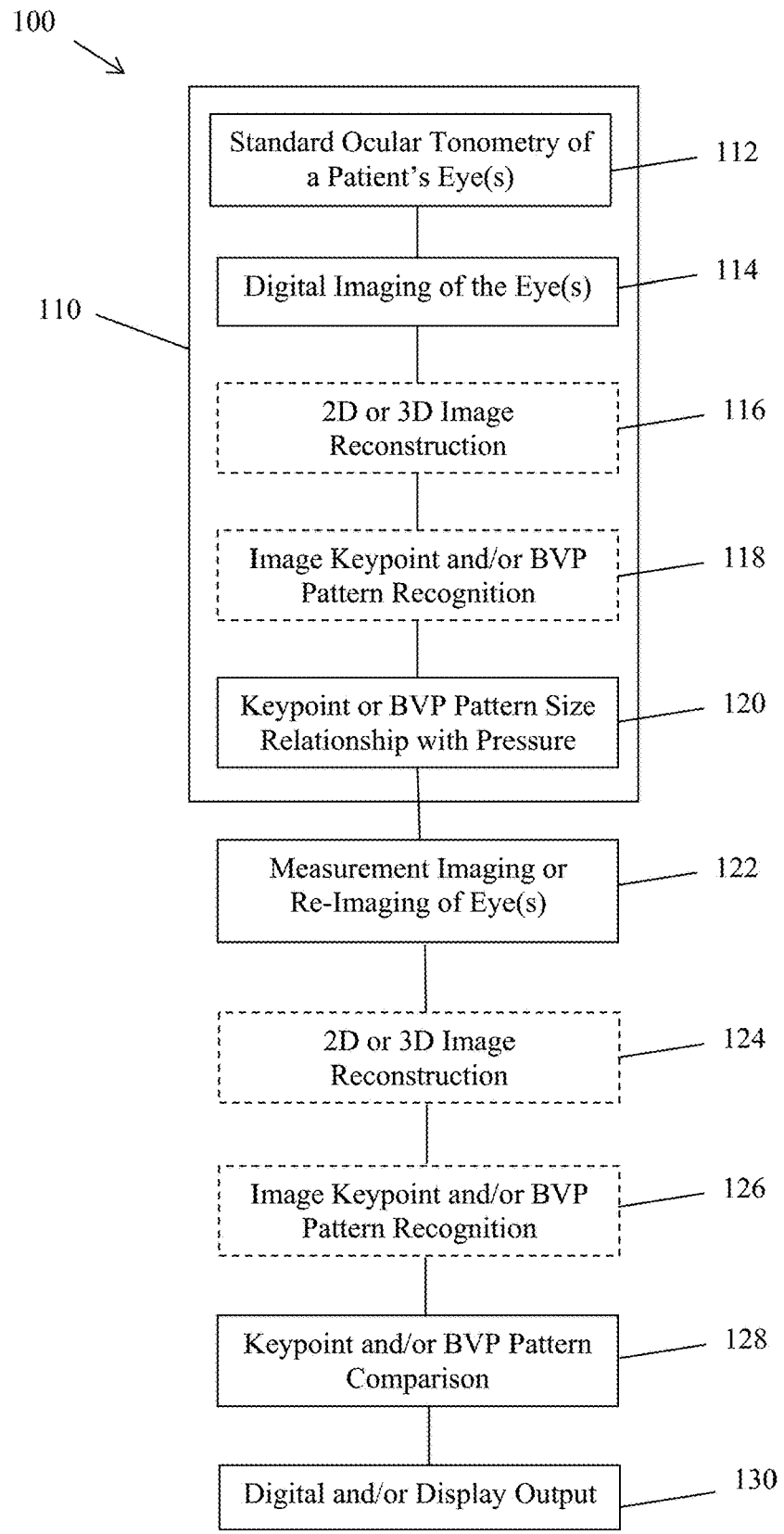
FIG. 1 is a flowchart detailing the subject medical method or diagnostic methodology.

FIG. 1 illustrates an example embodiment of the subject methodology 100. In the same seating or setting as the remaining method acts or steps, or in a prior appointment with an ophthalmologist, at 110 a set of calibration data (e.g., typically a minimum of two points for each eye of a given patient) are obtained. This is done using pressure modifying eye-drops standard tonometry is performed at 112. Digital imaging across the sclera of the eyes at 114 is also performed. The imaging captures the blood vessel pattern (BVP) against the contrast of the white sclera. A 2D or 3D image reconstruction may then be produced at 116. Next, keypoint (e.g, using SIFT software or other generic feature matching and stitching) and/or pattern recognition of the BVP at 118 my be performed. Together, at 120, these data are variously used (i.e., all such data may be used or a only a subset thereof used) to establish a pressure-BVP-size relationship. These acts (optionally taken together and performed in a separate procedure as indicated box 110) produce a calibration data set relating eye pressure to a the BVP across the sclera of at least on human eye.

After producing the calibration data set, one or both eyes are re-imaged or imaged for pressure measurement at 122. Such activity may be performed in the same setting or session (e.g., once a patient's ocular pressure is no longer influenced by the use of drops, or otherwise). Alternatively, it may occur at a later date in one or more follow-up visits to a clinic or other outpatient setting. Generally, such visits will be separated in time on the order of several months. In the case of monitoring for IOP change simply associated with volume and/or BVP scale change (each such case in which no calibration data is produced per step 110) or in the full method in which calibration data is employed, yearly changes may be observed over a patient's lifetime.

Each eye may be imaged in one scene or frame. Alternatively, in forming a so-called 2D or 3D "reconstruction," multiple scenes or frames may be "stitched" together to allow the an imaging system with a smaller field of view to interrogate the entire eye.

Either way, digital photography or videography may be so-employed. For 3D reconstruction, image processing at 124 (optionally as noted above using defocusing, blur-based imaging or stereo imaging) to form a 3D model will typically be employed. In 2D or 3D, the reconstruction process may also or alternatively involve using SIFT software to create (computer) identifiable keypoints involving or characterizing the included blood vessel patterns contrasted by or against the sclera.

In any case, at 126, pattern recognition techniques may then be applied to the 2D or 3D reconstruction characterizing the blood vessel pattern(s). At 128, keypoint and/or pattern matching of the output of either or both of 124 and 126 is performed, comparing to that produced or available from the calibration data set. The comparison (or comparisons, if additional scans are made of the eye after initial calibration data scanning) yields an estimation of scale change.

Together with the pressure-based calibration data, an estimated measurement of estimating IOP is produced as an output at 130. Otherwise, a comparison of overall volume change (eliminating the need for various keypoint or pattern recognition) and/or scale change BVP features can be made without involving calibration data. In which case, the comparison at 128 is between an earlier image data set and a current or later image data set and the output at 130 may be a relative indication of change in IOP (e.g., as an alert regarding climbing or escalating IOP). Any such output may be displayed on a monitor of such hardware as referenced below, stored in a patient file or otherwise handled.

Figure 2:
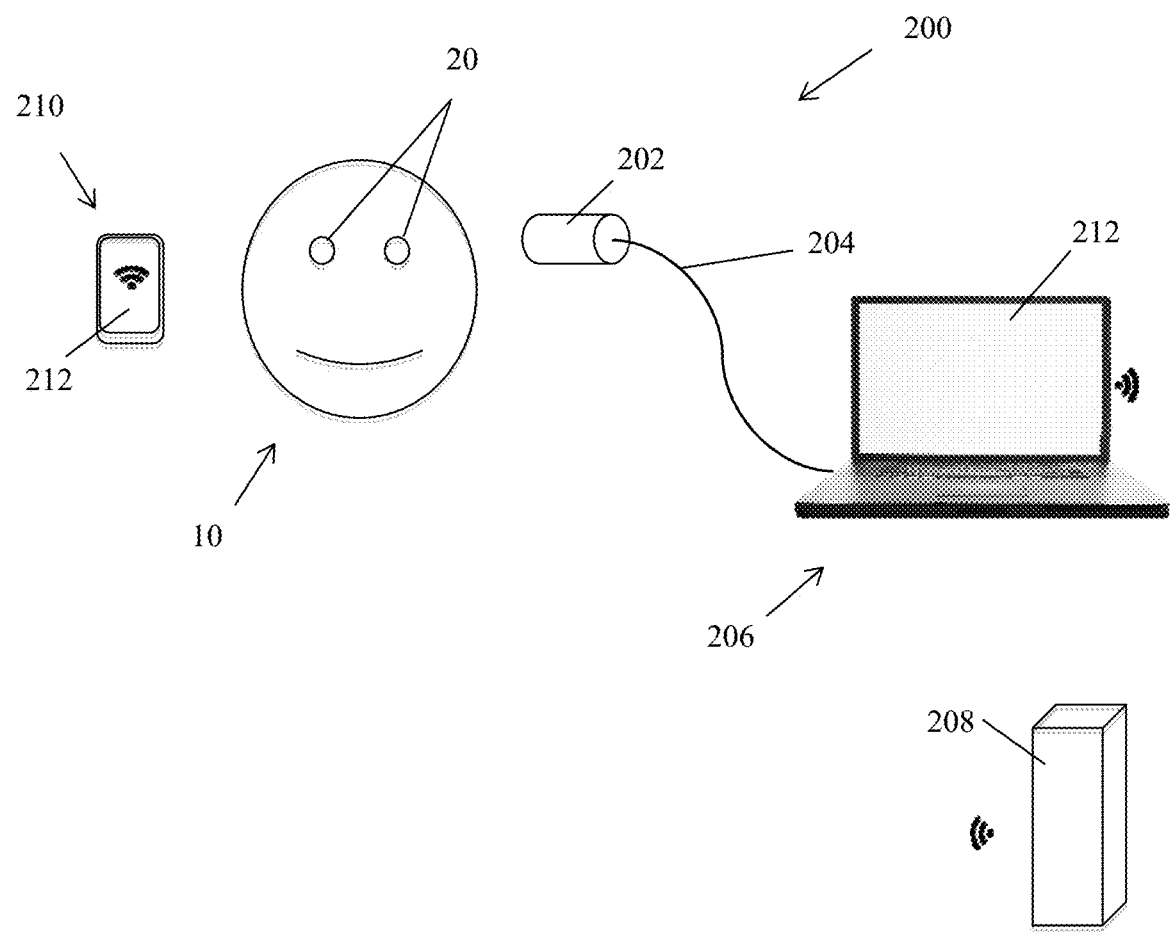
FIG. 2 is a diagram illustrating the associated hardware together with the subject human (or at least mammalian) anatomy.

FIG. 2 shows example embodiments of hardware options 200 together with a patient 10 and his or her eyes 20. The imager 202 may be a general purpose digital camera and/or may incorporate technology as described in any or all of U.S. Pat. Nos. 6,278,847, 7,612,870, 9,530,213 (naming Gharib as inventor) and U.S. Pat. No. 6,229,913 to Nayar, et al. These patents describe suitable hardware for 3-D imaging using various techniques. U.S. Pat. Nos. 6,278,847 and 7,612,870 describe so-called "defocusing" hardware and methods for determining 3D or depth information based on the separation of features imaged through offset apertures. U.S. Pat. Nos. 9,530,213 and 6,229,913 describe different hardware and methods for determining 3D or depth information from the relative blurring of different images having varying degrees of defocus (hereinafter "blur-based imaging"). These four patents are incorporated by reference herein in their entirety for all purposes. Alternatively, a stereo imaging camera system may be used for 3D determination. Stereo imaging systems are well known, with the SCANIFY system being a commercially available option.

Once the image data has been acquired, it can be transmitted over a data cable 204 (e.g., with a USB interface or otherwise) and the data can be stored locally (e.g., on a laptop computer 206). Alternatively, the data can be transmitted to (wirelessly—as indicated—or via wired connection) a remote server 208. As such, so-called "Cloud" computing may be employed. Likewise, digital image data that is acquired my be processed locally or it may then be processed remotely (e.g., by or in the Cloud).

In another embodiment, the entire approach may be implemented on or with a smartphone platform 210 (using its included camera and on-board processing componentry). Alternatively, the smartphone may be used for imaging and data display alone communicating wirelessly with the laptop computer 206 or network server 208 for additional processing resources.

In any case, the digital image sensor(s) are communicatively coupled to computer processing circuitry included in the system. Furthermore, non-transitory memory (variously located) provides storage for software to run the above processes. IOP-related indications, alerts, measurements or estimates that are generated from the digital image sensor data may communicated on any type of smartphone and/or computer display 212 or otherwise.

Variations

In addition to the embodiments disclosed already, still more variations are within the scope of this description. For example, the various illustrative methods or processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a digital camera of any type including those using CMOS, CCD or other digital image sensor or capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD or DVD, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available non-transitory media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

To the extent the embodiments disclosed herein include or operate in association with memory, storage, and/or computer readable media, then that memory, storage, and/or computer readable media are intended to be non-transitory. Accordingly, to the extent that memory, storage, and/or computer readable media are covered by one or more claims, then that memory, storage, and/or computer readable media is only non-transitory.

Operations as described herein can be carried out on or over a website or network. The website can be operated on a server computer or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., such as those already described. The programs may also be run over a network, for example, with a server or other machine sending signals to the local machine, which allows the local machine to carry out the operations described herein.

As used herein and in the appended claims, the singular forms "a", "an", and "the" include plural referents unless the context clearly dictates otherwise. In other words, use of the articles allow for "at least one" of the subject items in the description above as well as the claims below. The claims may exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The subject matter described herein and in the accompanying figures is done so with sufficient detail and clarity to permit the inclusion of claims, at any time, in means-plus-function format pursuant to 35 U.S.C. section 112, part (f). However, a claim is to be interpreted as invoking this means-plus-function format only if the phrase "means for" is explicitly recited in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An apparatus for intraocular pressure measurement, the apparatus comprising:
   a digital photography or videography system configured for three-dimensional imaging to capture blood vessel pattern images at a first instance to generate a calibration data set and at a second instance to generate a second data set;
   processing circuitry communicatively coupled with the digital photography or videography system; and
   non-transitory memory on which is stored:
   the calibration data set that comprises one or more images of blood vessel pattern;
   the second data set that comprises one or more images of blood vessel pattern; and
   a plurality of instructions that, when executed:
      assign scale-invariant feature transform (SIFT) keypoints to the one or more images of the calibration data set, the SIFT key points based on a blood vessel pattern (BVP);
      assign SIFT keypoints to the one or more images of the second data set; and
      cause the processing circuitry to estimate a change in intraocular pressure by comparing the SIFT keypoints of the calibration and second data sets based on a pressure-BVP-size relationship.

2. The apparatus of claim 1, wherein the blood vessel pattern is imaged at one of a sclera and a back of one or both eyes of a patient.

3. The apparatus of claim 1, wherein the non-transitory memory also stores a plurality of instructions that, when executed, cause the processing circuitry to compare the SIFT keypoints assigned to the measurement blood vessel pattern image with corresponding said SIFT keypoints assigned to the calibration blood vessel pattern image.

4. The apparatus of claim 3, wherein the non-transitory memory also stores a plurality of instructions that, when executed, cause the processing circuitry to estimate intraocular pressure scale differences between the SIFT keypoints.

5. The apparatus of claim 1, wherein the non-transitory memory also stores a plurality of instructions that, when executed, cause the processing circuitry to recognize and assign features of the measurement blood vessel pattern image.

6. The apparatus of claim 5, wherein the non-transitory memory also stores a plurality of instructions that, when executed, cause the processing circuitry to compare the features assigned to the measurement blood vessel pattern image with corresponding features assigned to the calibration blood vessel pattern image.

7. The apparatus of claim 6, wherein the non-transitory memory also stores a plurality of instructions that, when executed, cause the processing circuitry to estimate intraocular pressure scale differences between the features.

8. The apparatus of claim 1, wherein the configuration for three-dimensional imaging is selected from a configuration for defocusing imaging, blur-based imaging and stereo imaging.

* * * * *